United States Patent [19]

Barnes et al.

[11] Patent Number: 5,070,874
[45] Date of Patent: Dec. 10, 1991

[54] NON-INVASIVE DETERMINATION OF GLUCOSE CONCENTRATION IN BODY OF PATIENTS

[75] Inventors: Russell H. Barnes; Jimmie W. Brasch, Sr., both of Columbus, Ohio

[73] Assignee: Biocontrol Technology, Inc., Indiana, Pa.

[21] Appl. No.: 482,792

[22] Filed: Jan. 30, 1990

[51] Int. Cl.$^5$ .............................................. A61B 6/00
[52] U.S. Cl. ................................... 128/633; 128/664; 356/39
[58] Field of Search ............... 128/634, 633, 664, 665; 356/390, 40, 41

[56] References Cited

FOREIGN PATENT DOCUMENTS 0160768 11/1985 European Pat. Off. .

OTHER PUBLICATIONS

Yoshida, et al., "Spectrophotometric Monitoring of Arterial Oxygen Saturation in the Fingertip", Med. of Biological Eng. and Comput., 1980, 18, 27-32.

Primary Examiner—Francis Jaworski
Assistant Examiner—Scoh R. Akers
Attorney, Agent, or Firm—Hymen Diamond

[57] ABSTRACT

Radiation in the near infrared over a limited range of wavelengths about 1660 nanometers is projected on a portion of the body, for example, the ear, of the patient. The resulting radiation emitted by the portion, either scattered from the portion or transmitted after absorption and scattered by the portion, is process to derive an expression of the resulting radiation as a function of the wavelength. The second derivative of this function over a very narrow range of this function between 1640 and 1670 nanometers is expanded and the glucose concentration is determined from the magnitude, or intensity, of the scattered or transmitted radiation at the maximum or minimum point of this derivative. Apparatus for non-invasive determination of glucose concentration in the patient. Radiation in the near infrared is transmitted through a first fiber-optic radiation conductor to the outer surface of a portion of the patient's body, penetrating into the portion. A second fiber-optic conductor transmits the resulting radiation emitted from the portion to data processing means which produces the desired second derivative as a function of the wavelength of the incident radiation. The processor includes a spectrum analyzer which produces a spectrum of the resulting radiation.

13 Claims, 13 Drawing Sheets

NON-INVASIVE DETERMINATION OF GLUCOSE CONCENTRATION IN BODY OF PATIENTS

BACKGROUND OF THE INVENTION

This invention relates to the determination of the glucose in the blood of a patient who is suspected of suffering from diabetes or to control the treatment or medication of patients who already suffer from diabetes. It has particular relationship to such determination without drawing blood from the patient, i.e., by a non-invasive process and by non-invasive means.

There is widespread demand for non-invasive determination of glucose in patients. In the United States there are approximately ten million diabetics. Two million of these are Type 1 Diabetics, whose pancreas secretes no insulin; and eight million of these are Type 2 Diabetics, whose pancreas secretes insufficient insulin or secretes it too late. Most of the Type 2 Diabetics can be controlled with proper diet and weight control. Some of the Type 2 Diabetics and all of the Type 1 Diabetics require one or more shots of insulin per day. Insulin controls the body's utilization of glucose or sugar in the blood and, in the correct concentrations, prevents hyperglycemia (excess glucose) which, if left uncorrected, can lead to ketosis, coma and death. Glucose determination is also indispensible for sufferers from hypoglycemia who must ingest glucose containing fluids, such as orange juice, if the glucose in their blood decreases to a low level.

Hyperglycemia in the diabetic is strongly suspected of being responsible for the long-term effects of diabetes which include heart disease, arteriosclerosis, blindness, stroke, hypertension, kidney failure, and premature death. Severe hypoglycemia has similar drastic consequences. In a normal person, the blood glucose level may vary between 60 and 130 milligrams per deciliter, a variance exceeding 100%; whereas, in a diabetic, the levels may vary from time to time from 40 to 500 milligrams per deciliter, a variance of of 1150% for hyperglycemia. For hypoglycemia, 60 milligrams per deciliter indicates that treatment is necessary; the glucose may reach a dangerous level of 20 milligrams per deciliter. These large swings of glucose levels must be avoided to prevent the symptoms and complications of the disease. To avoid the swings, the diabetic must be able to conveniently monitor his blood glucose level, and then vary his caloric intake, diet and insulin to control the level. For effective control, frequent blood glucose monitoring is necessary.

The only practicable, reliable method currently available for monitoring blood glucose is by means of blood sampling. The diabetic pricks his epidermis with a needle, usually in the finger, draws a drop of blood, and absorbs the blood on a chemically treated strip of paper. He can then read the glucose level by placing the strip in a glucometer (a spectrophotometer which reads glucose concentrations); or he can compare the color change of the strip with a calibrated color chart. The direct reading instruments are more accurate. Other methods include measuring the electrical resistance of the strip with a glucometer which is an ohmeter calibrated in milligrams per deciliter. For effective control, some diabetics must utilize a finger prick four or more times a day.

It is desirable to dispense with the drawing and analyzing of blood and it is an object of this invention to achieve this purpose, providing for effective non-invasive determination of glucose concentration in a patient suspected to suffer from, or already suffering from, diabetes.

European Publication 0 160 768, dated Nov. 13, 1985, to Clause Dahne and Daniel Cross, is typical of the prior art relating to the non-invasive determination of glucose concentration. In Dahne, a beam of radiation in selected bands, 1575, 1765, 2100 and 2270±15 nanometers is impinged on a portion of the patient's body, penetrating into the portion, and the radiation resulting from the reaction within the body on the incident radiation is analyzed photometrically for the presence quantitatively of glucose. The resulting radiation which is analyzed may be scattered radiation or the transmitted radiation which, in effect, is the incident radiation less the predominant fraction of the scattered radiation and the radiation absorbed by the portion of the body.

Dahne suffers from the disadvantage that its process lacks the precision demanded for the effective monitoring of glucose concentration. The range of concentration over which the glucose is in practice monitored for effective control of the patient is between 40 and 500 milligrams per deciliter, but even lower concentrations may be encountered in hyperglycemia or hypoglycemia. A concentration appreciably greater than 120 milligrams per deciliter indicates a diabetic condition and treatment by diet or insulin. In the actual practice of Dahne's process, the highest concentration of glucose which was measured was one molar (1M) and the lowest concentration of glucose which was measured was 0.05 molar (page 18). The chemical formula for glucose is $C_6H_{12}O_6$. In a 1M solution of glucose, there are 180.16 grams per liter or 18,000 milligrams per deciliter. In 0.05 mole, there are 0.9 grams or 900 milligrams per deciliter. This is far out of the range of glucose concentrations which must be measured for effective control and, indeed, out of the range which is compatible with life. There is no evidence in Dahne that its process is more effective than is indicated by its tests.

It is accordingly an object of this invention to overcome the disadvantages and drawbacks of the prior art and to provide for the precise effective non-invasive determination of the concentration of glucose in a patient, taking into consideration the concentrations actually involved in such determination.

SUMMARY OF THE INVENTION

This invention arises from the realization that in any expression, for example, in a graph, of the concentration of glucose in blood as a function of the wavelengths over which an analysis is carried out, the measure of the maximum concentration, which must be precisely determined, is often obscured by the presence of other chemical species. It has been realized in arriving at this invention that the specific species which must be measured may be emphasized and readily determined by deriving a new function, the nth derivative with respect to wavelength of the expression defining the concentration of glucose as a function of wavelength, over a defined region of this nth derivative. Once the magnitude of the nth derivative with respect to a zero reference is determined, this magnitude may be converted into glucose concentration by reference to the magnitude for log 1/T the known specimens and the appropriate derivatives corresponding to these known specimens, i.e., by calibrating the apparatus with known specimens containing known concentrations of the species to be measured.

$$T = \frac{I_o}{I}$$

where $I_o$ is the intensity of the radiation incident on the portion of the patient's body and I is the resulting radiation transmitted through or scattered by the portion.

In the specific practice of this invention, the concentration of the glucose is evaluated at or near the maximum or minimum of the second derivative of log 1/T as a function of the wavelength, but other points along the function may be selected in accordance with this invention. In particular, the evaluation may be taken at a point displaced from a reference point or region which may be referred to as a "crossover" point or region. The crossover region is the region in which functions for a large number of spectra intersect. The evaluation may be taken at a convenient point sufficiently displaced from this region to yield a reliable measurement of the concentration for a specimen. Advantageously, the selected evaluation point or region may be a maximum or minimum point since, at this point, there is a maximum displacement in concentration either positively or negatively from the crossover point. An evaluation point may also be selected based on statistical determination of the maximum coefficient of correlation along an expression or function between known spectra and the functions serving as a basis for comparison.

Specifically, the non-invasive measurement of the concentration of glucose in blood is performed with a near-infrared radiation source, a fiber-optic probe, a spectrum analyzer with a detector and a data processor. The fiber-optic probe consists of a dual conductor of near infrared radiation which is used in either the transmission or scattering mode. Radiation from the near infrared source is transmitted through one of the dual conductors, the end of which is placed in contact with a portion of the patient's body. The radiation transmitted into the body undergoes scattering and characteristic absorption depending on the identity of the species present. A portion of the radiation having undergone scattering and absorption is back scattered from the body and collected and transmitted back to the spectral analyzer/detector system by the other fiber-optic conductor. The sensing end of the fiber-optic probe, placed in contact with the body, is arranged so that either a transmission or a scattering measurement is performed. In the transmission mode, the sensing end of the fiber-optic probe is arranged so that the near infrared radiation from the source can be passed through the portion of the body which may be the ear lobe, tongue or webbing between the fingers or toes and its spectral absorption characteristics measured. This is accomplished by placing the body section between the opposite ends of the dual fiber so that radiation from the fiber-optic conductor connected to the near infrared source passes through the body section to the other fiber-optic conductor which transmits the attenuated radiation to the spectral analyzer/detector. In the scattering mode, a bifurcated fiber-optic probe is used. The bifurcated probe consists of two separate bundles of fibers, one bundle being centrally located and the other bundles being disposed in any configuration surrounding the central bundle. To measure blood glucose, the sensing end of the probe is placed in direct contact with an outer surface of the body. Near infrared radiation from the fibers connected to the source is transmitted through that portion of the body undergoing both characteristic spectral absorption and scattering. Some of the scattered radiation which has traveled through the body experiencing absorption is collected by the optical fibers in the configuration and then transmitted to the spectrum analyzer/detector.

The spectrum analyzer for this application can consist of a dispersive spectrometer with a prism or diffraction grating, a set of optical filters, a scanning interferometer, a stationary interferometer, or it may consist of a Hadamard transform spectrometer. Hadamard transform spectroscopy is described in a paper by Hammaker et al. in *Vibrational Spectral and Structure*, Vol. 15, Nov. 1986, edited by J. R. Durig, Elseviere Press, Amsterdam, Holland. Spectrometers are disclosed in Fateley patents U.S. Pat. No. 4,615,619, U.S. Pat. No. 4,750,834 and U.S. Pat. No. 4,799,795. The purpose of the spectrum analyzer is to disperse the near infrared radiation passing through the body into its spectral components to distinguish and quantify those particular spectral components that are characteristic of blood glucose. The characteristic near infrared absorption by the glucose can be related directly to its concentration in blood.

The data processor receives the output signal from the spectral analyzer, calculates the concentration of blood glucose, and formats the output to a display or recording device giving blood glucose concentration in selected units. A microprocessor in the data processor is used to perform data processing and control the operation of the spectral analyzer.

To investigate and demonstrate the practical utility of the invention, near infrared measurements were performed in water and different concentrations of glucose in water, blood plasma, whole blood and different concentrations of glucose in whole blood, human ears, and rabbit ears. It was found that the second derivative of the expression for the absorption of the radiation as a function of wavelength about the near infrared band of glucose near 1660 nm, which occurs on the side higher-frequency of the water-absorption band at 1450 nm, yielded effective data from which precise concentration could be derived. In the practice of this invention, in its broad aspects, measurements are made over the range of wavelengths from 700 to 3000 nm.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which:

FIG. 6 is a graph similar to FIG. 4 in which the concentration of glucose in blood plasma, determined in the practice of this invention from the data on which FIG. 5 is based, is plotted against the corresponding known concentrations.

FIG. 9 is a graph similar to FIGS. 4 and 6 in which the concentration of glucose in water, determined in the practice of this invention from the data on which FIGS. 7 and 8 is based, is plotted against the corresponding known concentrations;

FIGS. 10 and 11 are based on FIG. 12.

DETAILED DESCRIPTION OF INVENTION

Figure 1:
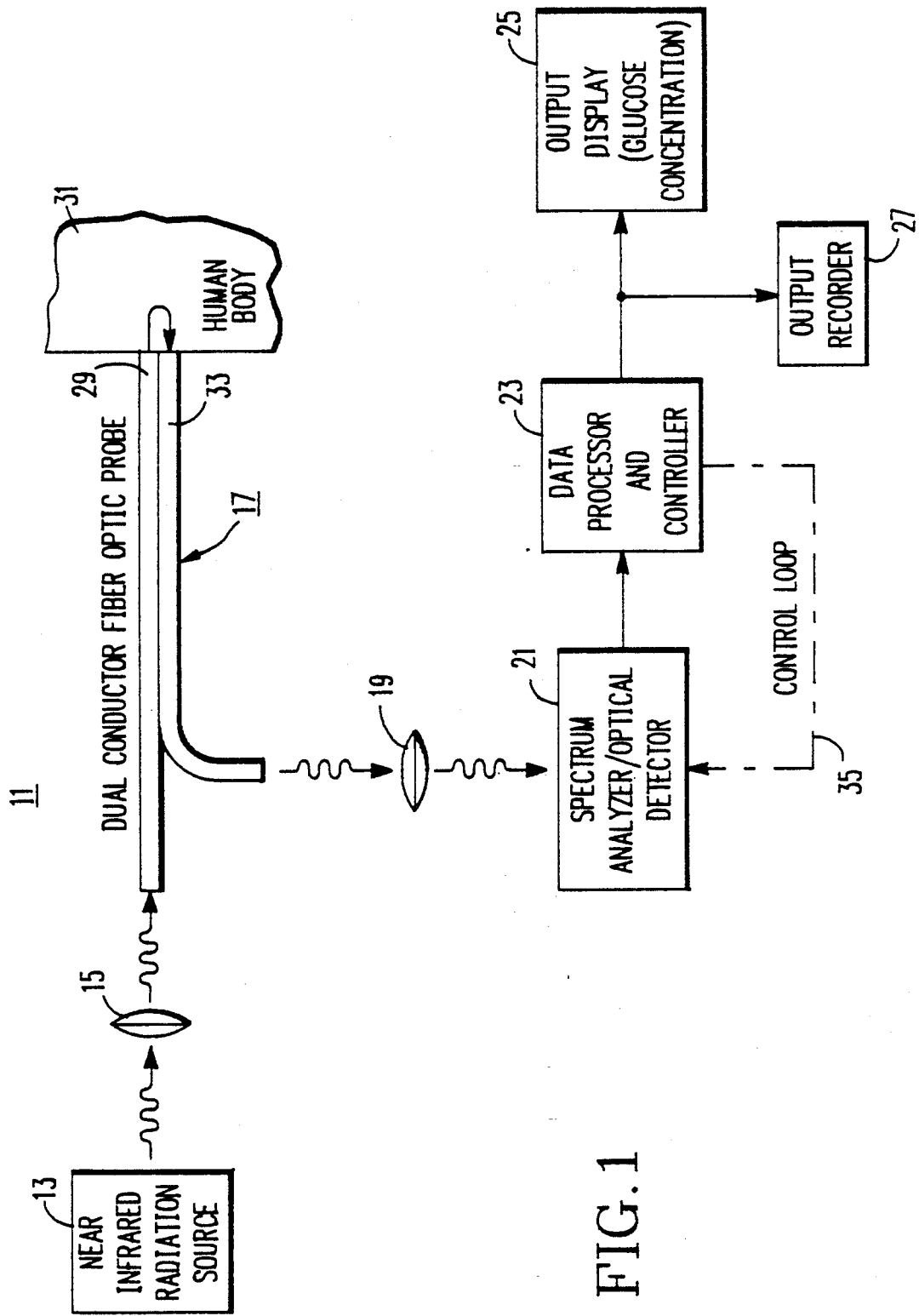
FIG. 1 is a block diagram showing an embodiment of this invention with which the method of this invention is practiced.

FIG. 1 shows apparatus 11 for the non-invasive determination of the glucose concentration in a patient. This apparatus includes a source 13 of near-infrared radiation, a lens system 15, a dual conductor fiber-optic probe 17, a second lens system 19, a spectrum analyzer/detector 21, a data processor and controller 23, an output display device 25 and an output recorder 27. As stated the source may produce radiation over the range from 700 to 3000 nm. The data presented in this application was produced using a Model 6250 System Near Infrared Spectrometer acquired from Pacific Scientific Instrument Division of Pacific Scientific, Ltd. The address of this Instrument Division is 2431 Linden Lane, Silver Spring, MD 20910. The lens systems 15 and 19 are represented by single-lens symbols. In actual practice, they are appropriate combinations of lenses including focusing lenses and collimators on the outlet side. The fiber-optic probe 17 includes an input radiation conductor 29 for transmitting radiation to a portion 31, for example, an ear lobe or wrist, of the patient's body and an output radiation conductor 33 for deriving the resulting radiation from the portion 31. The output end of the input conductor 29 and the input or sensing end of the output conductor 33 are in firm contact with the outer surface of the portion 31 of the patient's body. While each conductor 29 and 33 is represented by a symbol for a single conductor, each radiation conductor, in actual practice of this invention, includes bundles of optic fibers.

Radiation from the source 13 is directed by the lens system 15 into conductor 29 and, at its outlet, is projected into the portion 31. This incident radiation induces scattered radiation within the body portion 31, some of which passes through the end of conductor 33 and through the conductor and is directed by lens system 19 into the spectrum analyzer/detector. While FIG. 1 discloses apparatus in which scattered radiation is analyzed, the analysis of transmitted radiation, i.e., the input radiation less the back scattered and absorbed radiation, plus any forward scattered radiation, is within the scope of equivalents of this invention. In this case, the ends of conductors 29 and 33, instead of being side-by-side in contact with adjacent surfaces of the body portion 31, would be in contact with the outer surfaces on opposite sides of the body portion 31, for example, with opposite surfaces of the ear lobe. The radiation, which is in this case passed through conductor 33, is predominantly the radiation from the source 13 less the radiation scattered and absorbed by the molecules of the water in the blood, the glucose and other constituents of the blood. The skin also contributes to the scattering and absorption.

With the apparatus as shown in FIG. 1, the resulting back scattered radiation emitted by the body portion 31 is passed by output conductor 33 and lens system 19 to the spectrum analyzer/detector 21 where this radiation is spread into a spectrum consisting of the wavelength distribution of the radiation intensity. This radiation is converted by an optical detector to electrical signals which are transmitted to the data processor 23. The operation of the spectrum analyzer in producing the spectrum is coordinated with the operation of the data processor through feedback channel 35, so that for each wavelength the data processor produces an electrical signal whose magnitude corresponds to the intensity of radiation at each wavelength. In this way an expression or spectrum of the resulting scattered radiation as a function of wavelength characteristic of the glucose concentration is produced. This expression appears on the output display 25 and is entered in the output recorder 27. In accordance with this invention, in its broader aspects, the data processor computes the nth derivative of the expression or spectrum expanded over a small subrange of wavelengths of the function defining the expression at a correlated point selected by statistical multi-variant calibration procedures. The glucose concentration is determined from the magnitude of the absorption, i.e., the reciprocal of the transmission, at this point and the relationship of the absorption, to concentration at this point as determined by calibration. In the specific practice of this invention as disclosed herein, the determination is simplified by computing the concentration at a maximum or minimum point of the second derivative, i.e., near a maximum or minimum point of the function itself. The minimum is preferred because in this region the transmission is a maximum.

EXAMPLE

Figure 2:
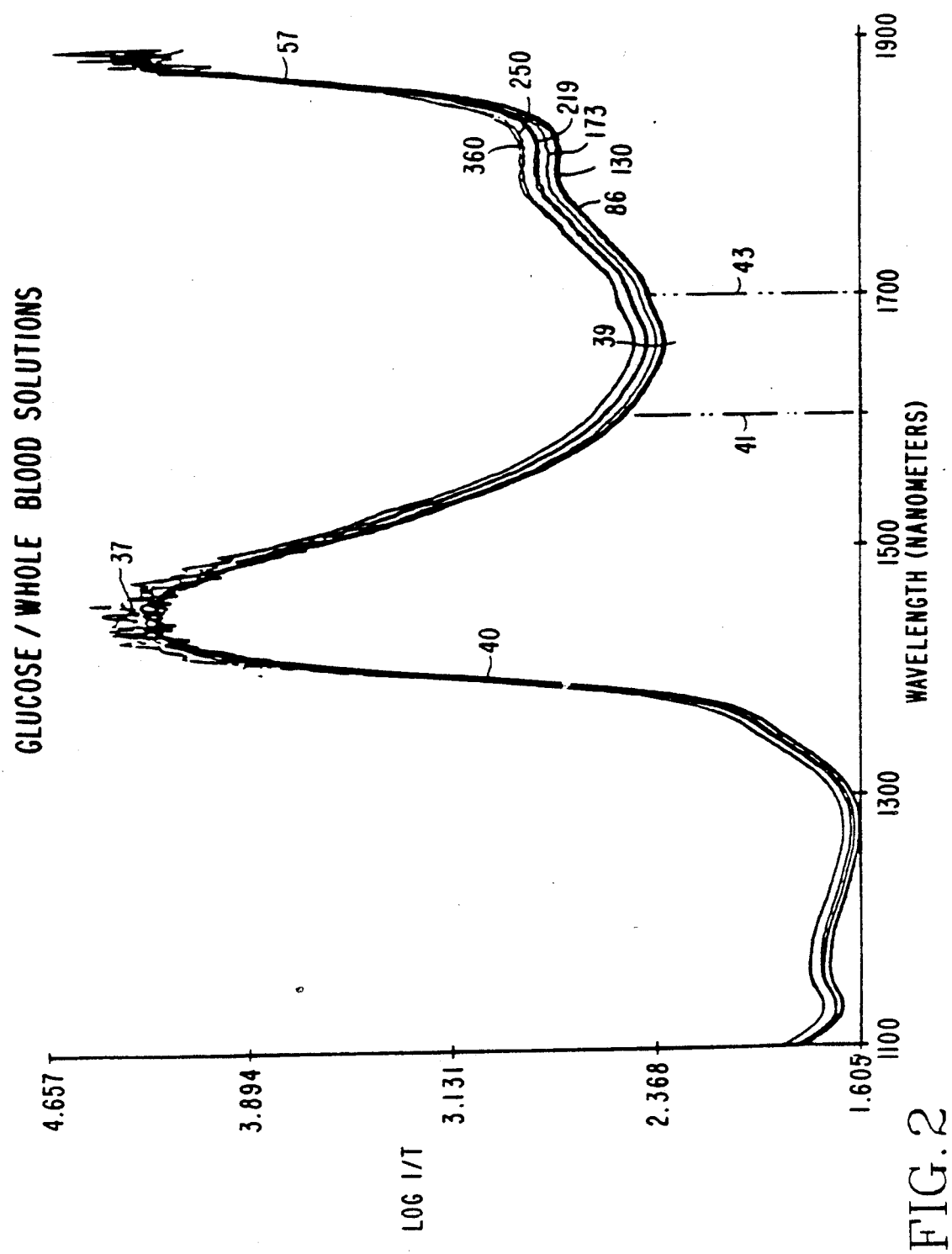
FIG. 2 is a graph presenting the log of the reciprocal of the transmission of radiation through specimens, i.e., the absorption for the specimens, as a function of the wavelength in the near infrared for whole-blood solutions of different concentrations of glucose.

A number of samples of blood were taken from one of the applicants and an associate. Neither man suffers from diabetes. The samples were doped with glucose of the concentrations in milligrams per deciliter shown in FIGS. 2 and 3. Each sample was analyzed as described above in a Yellow Spring Instrument glucose analyzer. The near infrared measurements were performed using the Pacific Scientific Model 6250 linear infrared spectrometer. The absorption method was used. Radiation in the near infrared was transmitted through each sample and an expression or spectrum was produced, as shown in FIG. 2. In this view, 1/T is plotted vertically as a function of wavelength plotted horizontally.

$$T = \frac{I}{I_o}$$

where I is the intensity of the radiation transmitted or the transmission through the sample, $I_o$ is the intensity of radiation incident upon the sample.

$$\text{Log}\frac{1}{T} = \text{Log}\frac{I_o}{I}$$

The plot is over the limited range between 1100 and 1900 nanometers. FIG. 2 shows a family of curves or spectra for the different concentrations of glucose in the blood which were measured. The curves are labeled to show the concentrations, the numbers 86, 130, 173, 219, 250, 360 are in milligrams per deciliter. FIG. 2 has two sets of stationary points, 37 a maximum and 39 a minimum. In the region 40, between the minimum near 1300 nm and the maximum 37, there is a crossover region. The maximum points 37 correspond to low magnitudes of I and the minimum points to high magnitudes of I. The minimum points 39 identify a frequency at which the transmission for the various concentrations is a maximum.

Figure 3:
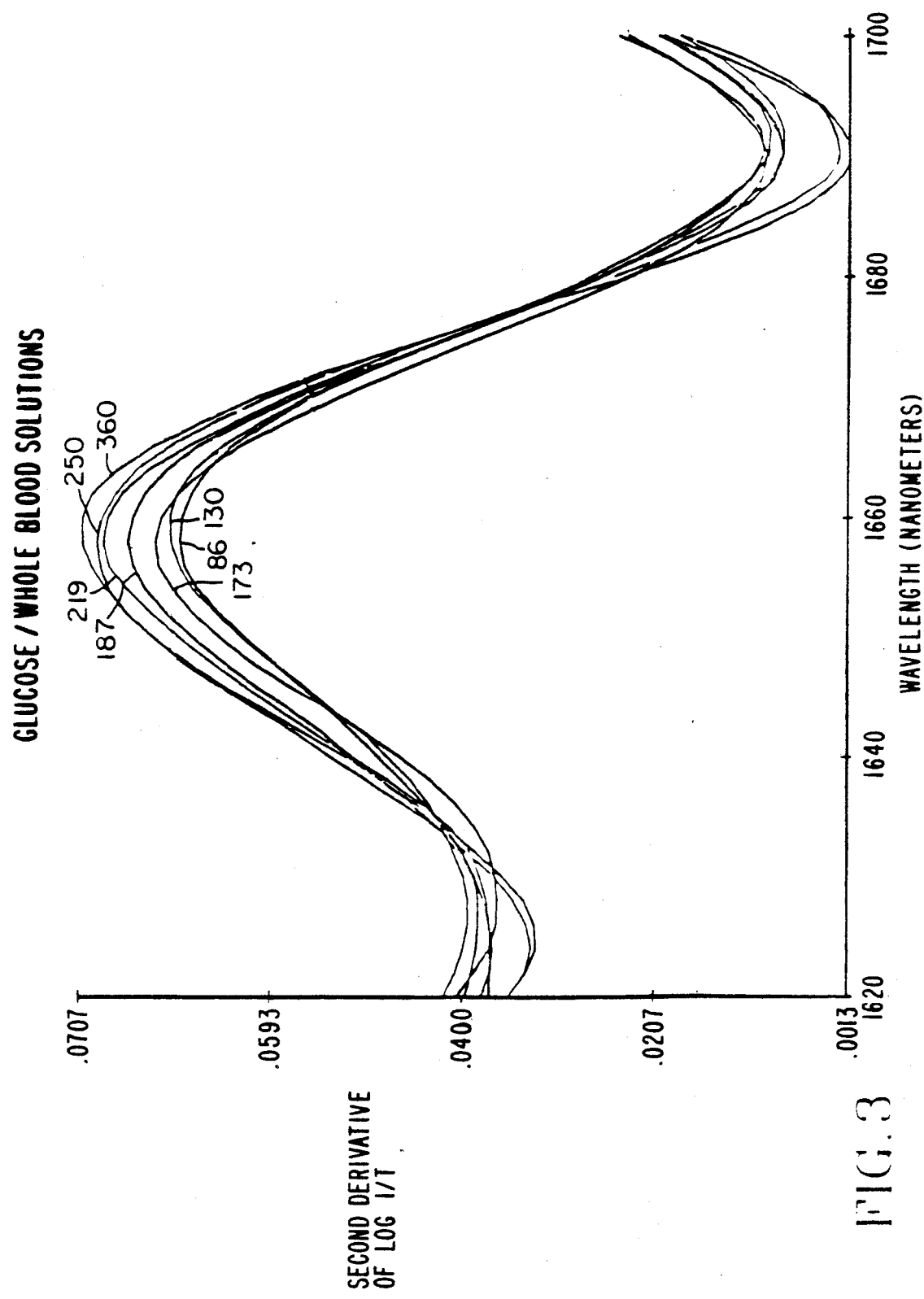
FIG. 3 is a graph presenting the second derivative of the function shown in FIG. 2 as a function of wavelength expanded over a small subrange of the wavelengths of FIG. 2.

It was found by further analysis that, in the region of this minimum region 39, the concentration of the glucose is readily determinable. The second derivative was determined for the very narrow subregion between lines 41 and 43, corresponding to wavelengths 1620 and 1700 nanometers and a highly blown up or enlarged display of this function was produced. This graph is shown in FIG. 3. The second derivative of log 1/T, as a function of wavelength, is plotted vertically and wavelength horizontally. The enlargement results in a family of curves, one for each concentration, as indicated. The maximum points of these curves are at about 1660 nanometers. FIG. 3 shows that in the region 44 of the maximum of the second derivative, at 1660 nanometers, there is a substantial spread between the curves. The spread provides a convenient scale for determining glucose concentration.

Figure 4:
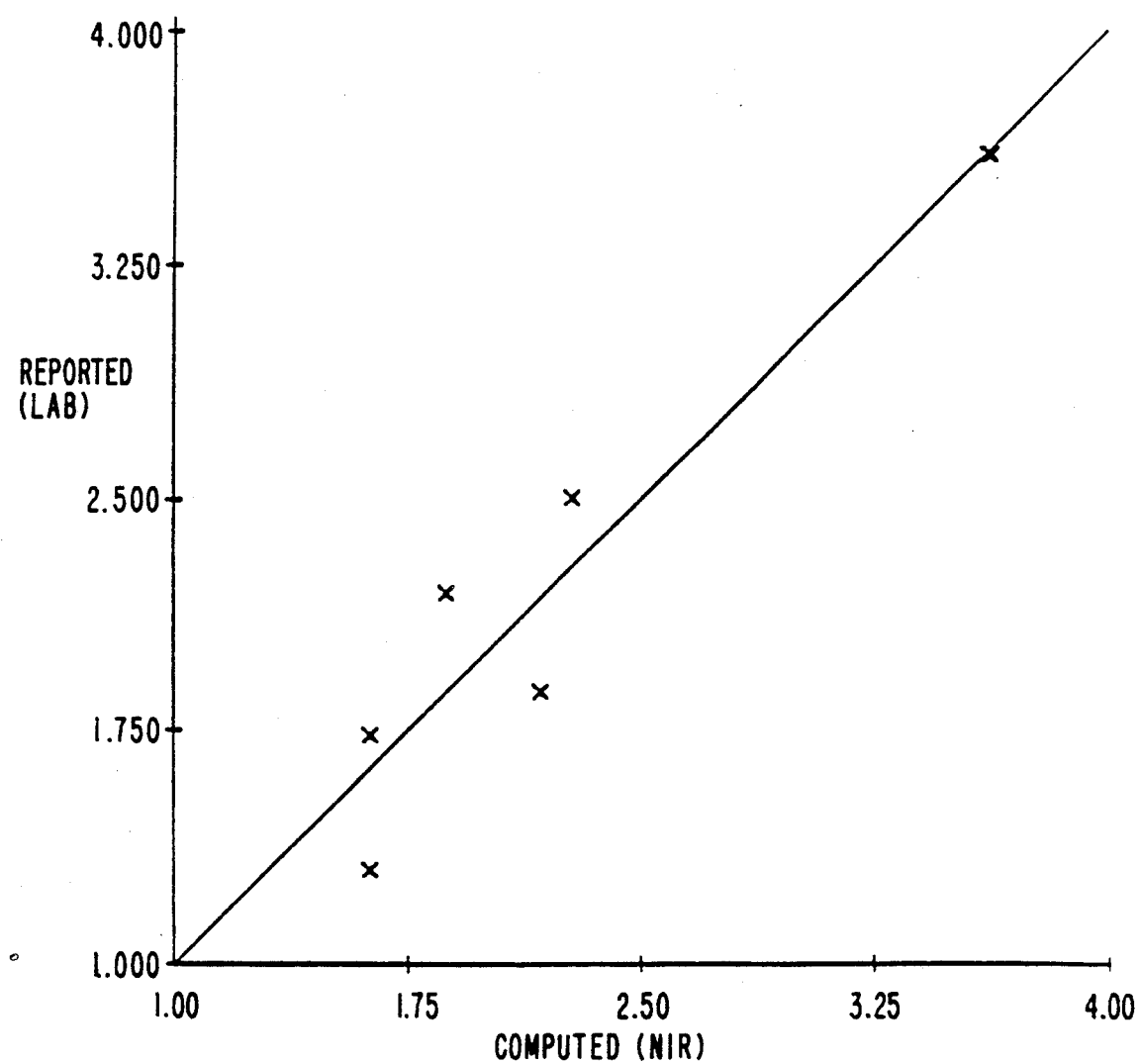
FIG. 4 is a graph in which the concentration of glucose in whole blood determined in the practice of this invention from the data derived from the graph shown in FIGS. 2 and 3 is plotted against the corresponding known concentrations.

To evaluate the reliability of the practice of this invention, the glucose concentration of the samples was determined by conventional methods and compared with the concentrations measured in the practice of this invention. The measured concentrations were derived by the data processor at wavelength of about 1660 nanometers. In FIG. 4 the known concentration is plotted vertically in $10^2$ milligrams per deciliter and the measured concentration is plotted horizontally in $10^2$ milligrams per deciliter. In the resulting graph, the 45° line shows that there is a precise correspondence between the actual concentrations and the concentrations measured in the practice of this invention.

By the process in accordance with this invention as described above, concentrations of glucose in the range actually encountered in diabetics can be precisely measured. In practice, an expression such as is shown in FIG. 3, or a like expression for scattering rather than transmission, may be entered into the memory of data processor 23 of the apparatus shown in FIG. 1. A patient suspected of suffering from diabetes is subjected to non-invasive testing as disclosed with reference to FIG. 1. The resulting second derivative of the expression of log 1/T as a function of wavelength is evaluated against the expression in the memory of the computer to determine the glucose concentration of the patient. Alternatively, a narrow region of the graph corresponding to FIG. 2 for the patient may be blown up in the critical region shown by the graph corresponding to FIG. 3 for the patient and the concentration computed from log 1/T at the minimum point.

Figure 5:
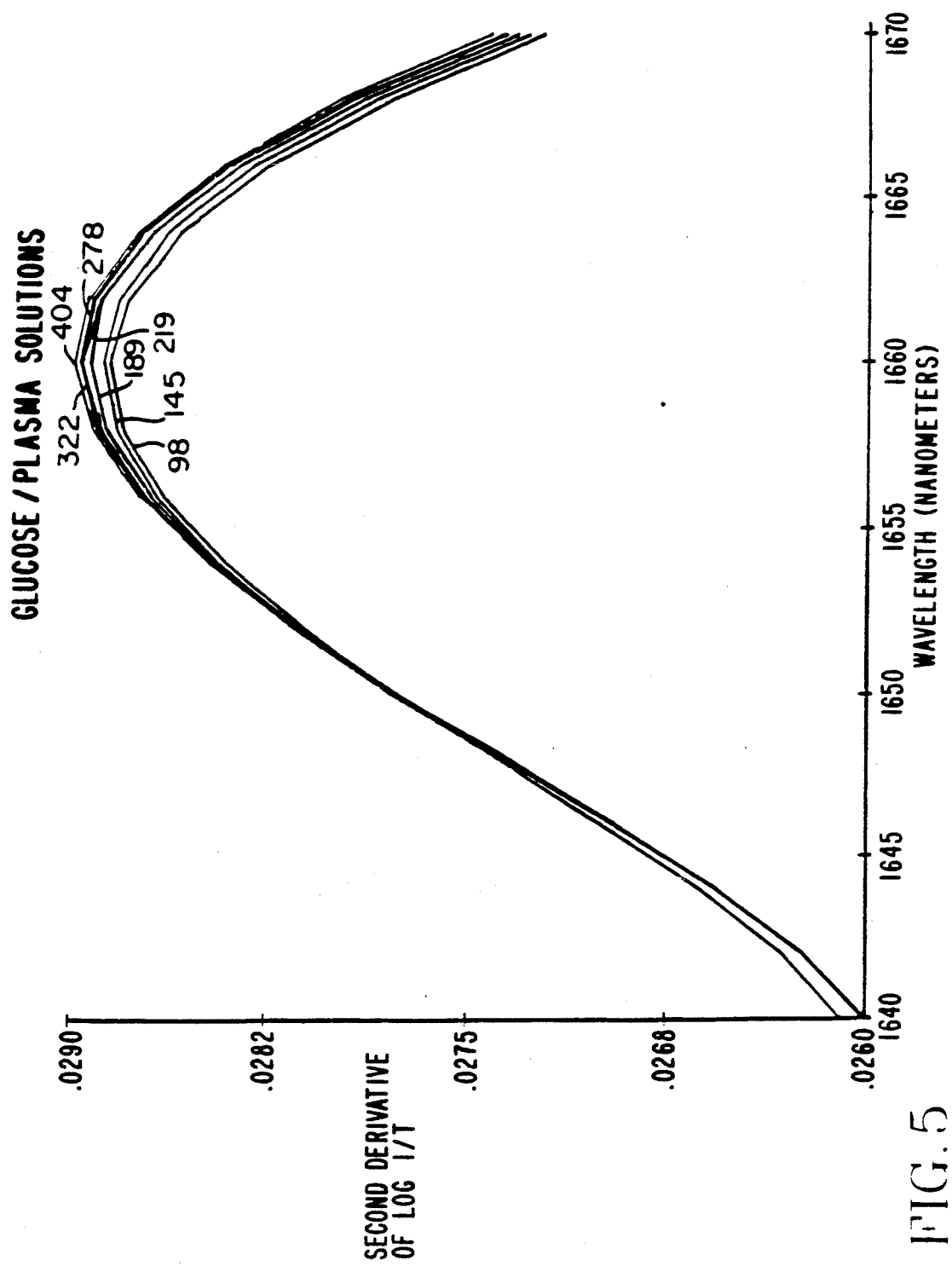
FIG. 5 is a graph similar to FIG. 3 presenting expanded over a small wavelength range the second derivative of the log of the reciprocal of the transmission of radiation through specimens as a function of the wavelength from different concentrations of glucose in blood plasma.
Figure 6:
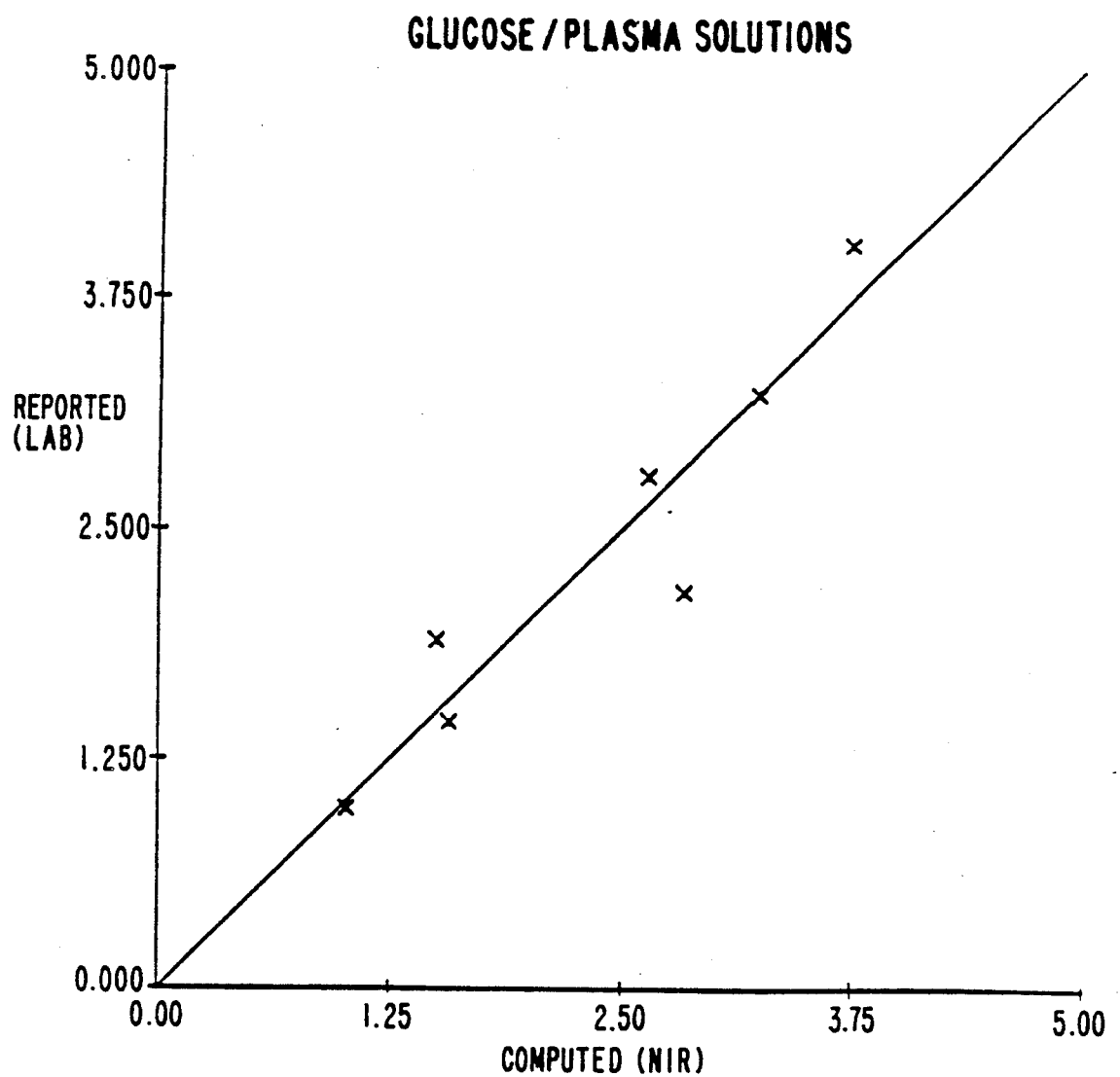

FIG. 5 is a graph in which the second derivative of log 1/T is plotted as a function of wavelength for various concentrations, 98, 145, 189, 219, 278, 322 milligrams per deciliter, of glucose in blood plasma. In this case again, there is a substantial spread between the curves for the different concentrations at the maximum in the region of 1660 nm. FIG. 6 shows that, in this case also, there is close correlation between the concentrations computed from FIG. 5, plotted horizontally, and the known concentrations, plotted vertically. The concentrations are expressed in $10^2$ milligrams per deciliter.

Figure 7:
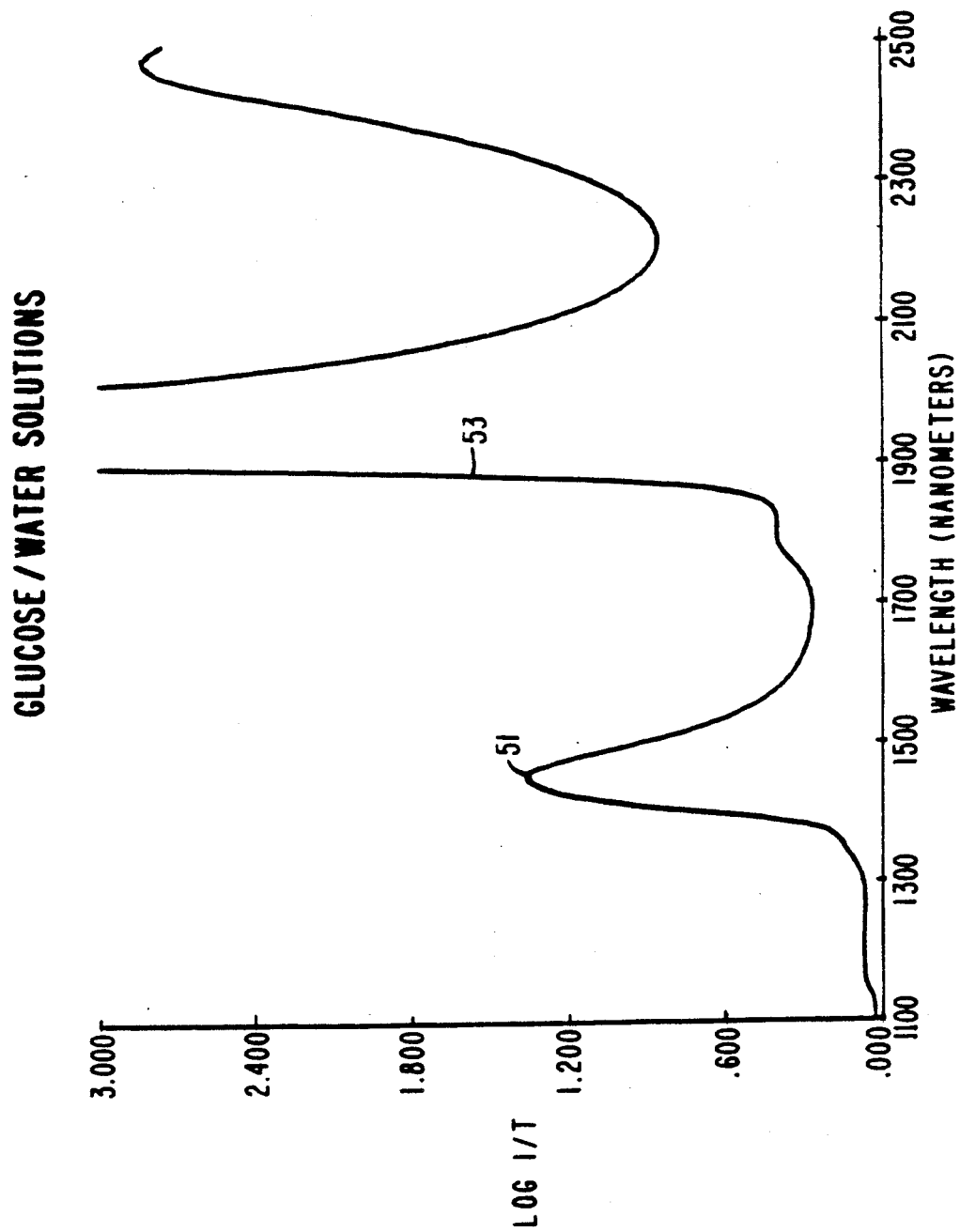
FIG. 7 is a graph showing as a single line the log of the reciprocal of the transmission of radiation through specimens as a function of the wavelength for water solutions of different concentrations of glucose.

FIG. 7 is a single line graph in which log 1/T is plotted vertically against wavelength plotted horizontally for several concentrations of glucose in water. This graph is significant because the major component of animal blood is water. The similarity between FIG. 7 and FIG. 2 is striking. FIG. 7 has a maximum 51 between about 1400 and 1500 nm and a sharp rise 53 at about 1900 nm. These regions correspond to the maximum 37 and the sharp rise 57 in FIG. 2.

Figure 8:
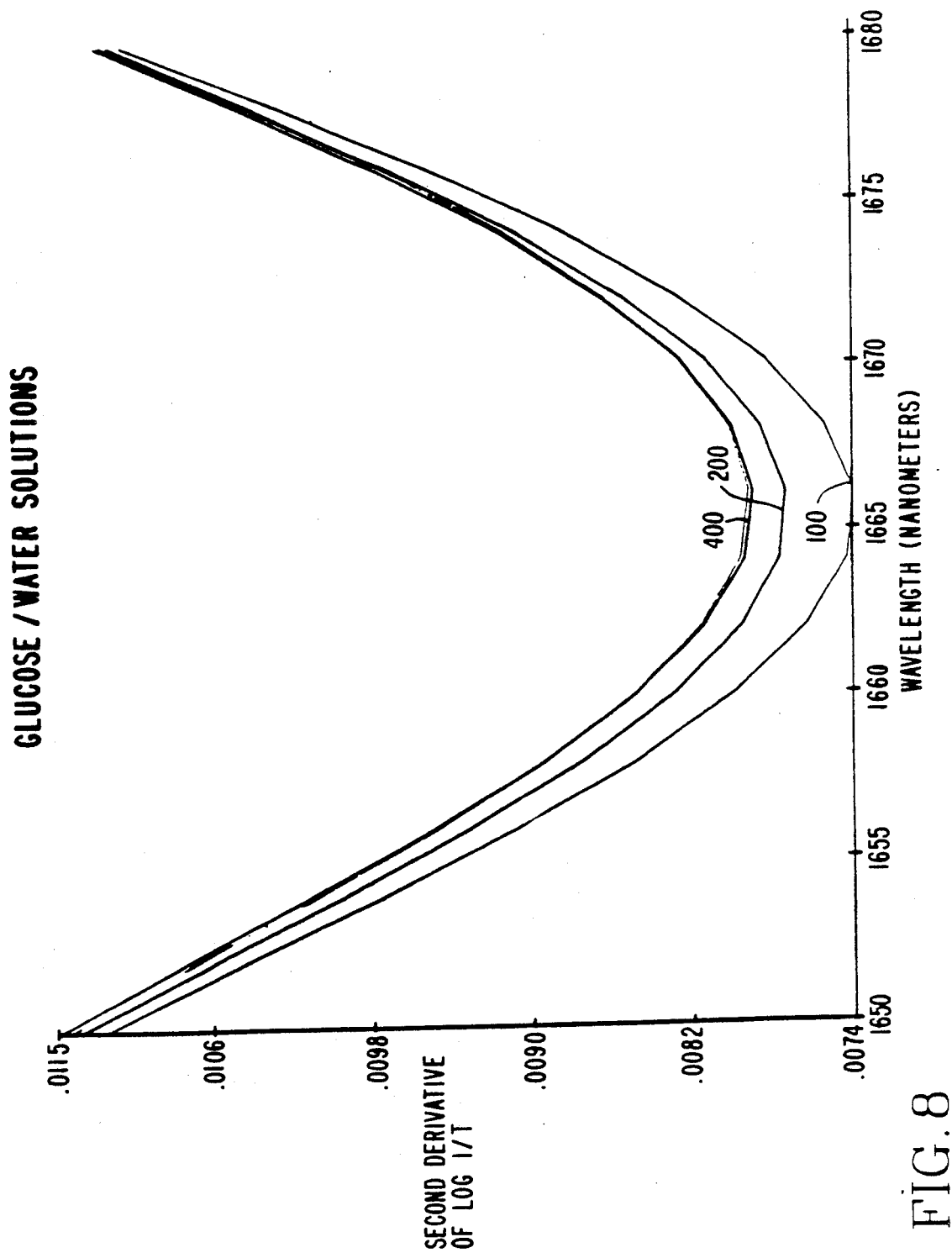
FIG. 8 is a graph similar to FIG. 3 presenting expanded over a small wavelength range the second derivative of the functions shown in FIG. 7 as a function of wavelength.

In FIG. 8 the second derivative as a function of wavelength of the function in FIG. 7 is plotted in wavelength range between 1650 nm and 1680 nm. This range is near the minimum 61 at about 1680 nm of the function shown in FIG. 8. The spread near 1665 nm between the curves for the different concentrations is notable. The numbers shown in FIG. 8 are in milligrams per deciliter.

Figure 9:
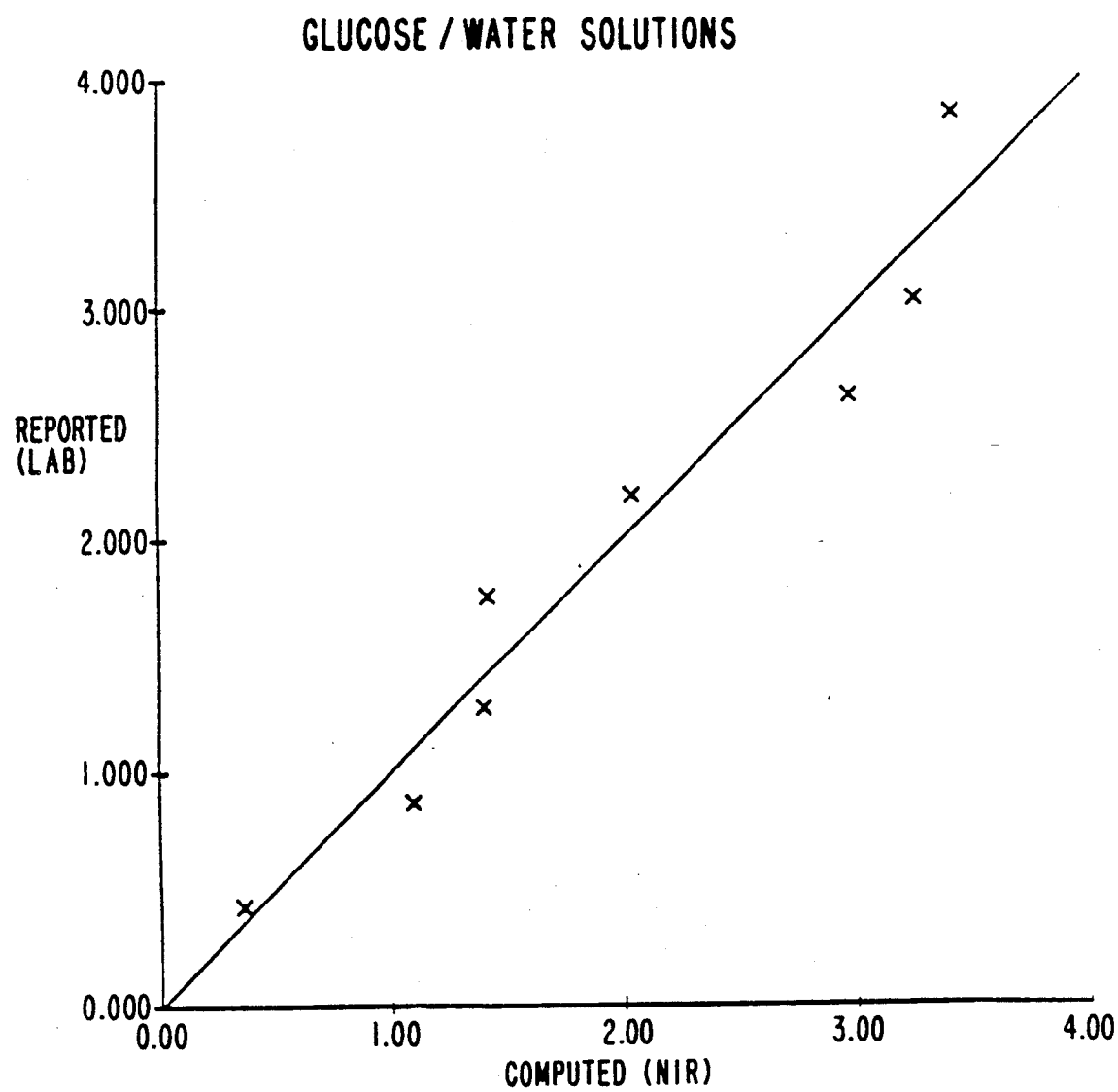

FIG. 9 shows the close correlation between the known concentrations and the measured concentrations.

Figure 10:
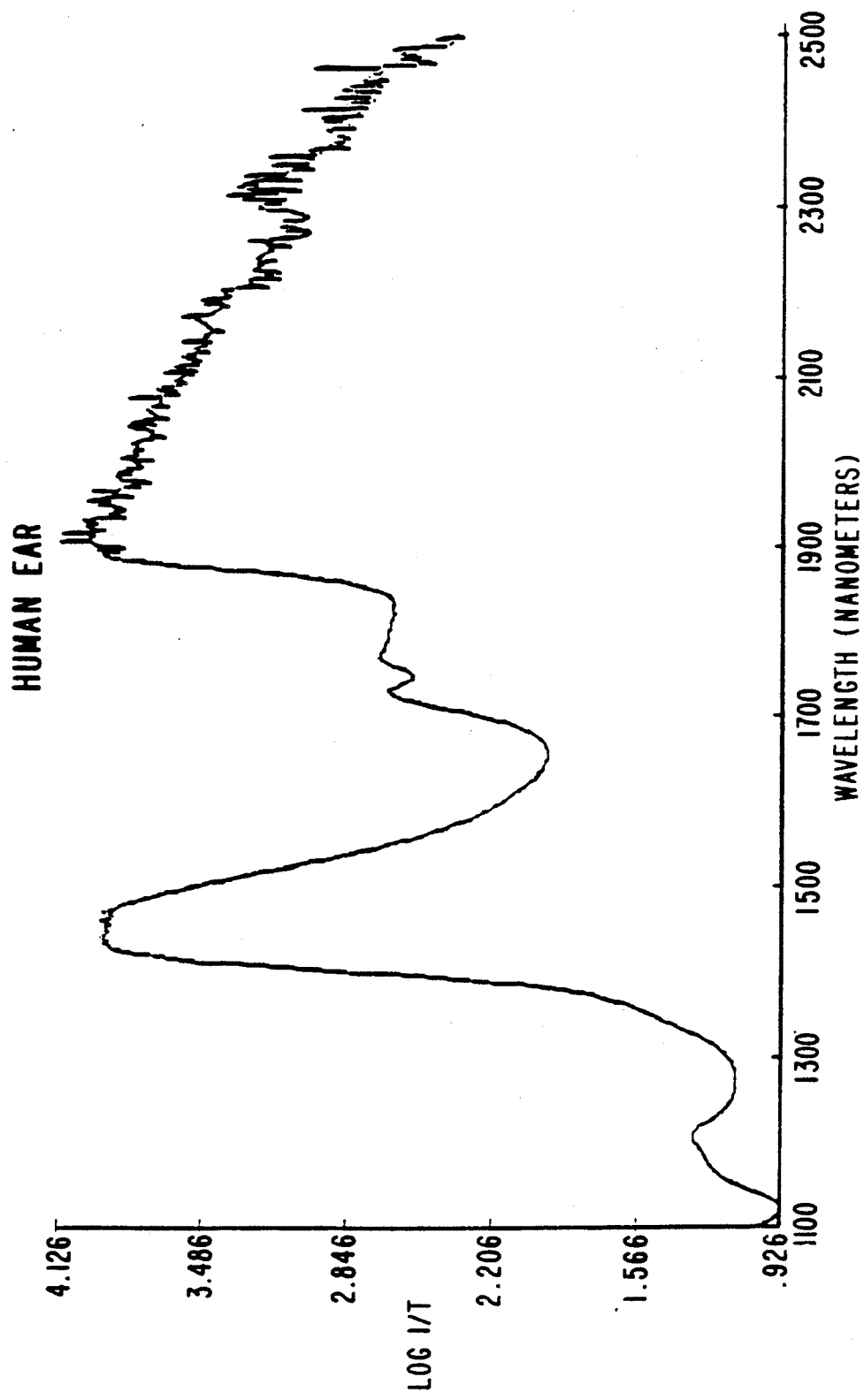
FIG. 10 is a graph presenting the reciprocal of the log of radiation in the near infrared through the ear of a human host as a function of wavelength after ingestion by the host of glucose.

FIG. 10 is based on data produced by actual measurement, with the apparatus according to this invention, by transmission of radiation through the ear of a host of the concentration of glucose as a function of wavelength after ingestion of 75 grams of glucose by the host. In FIG. 10, log 1/T is plotted vertically and the wavelength horizontally. The similarity between FIGS. 2 and 7 and FIG. 10 is significant.

Figure 11:
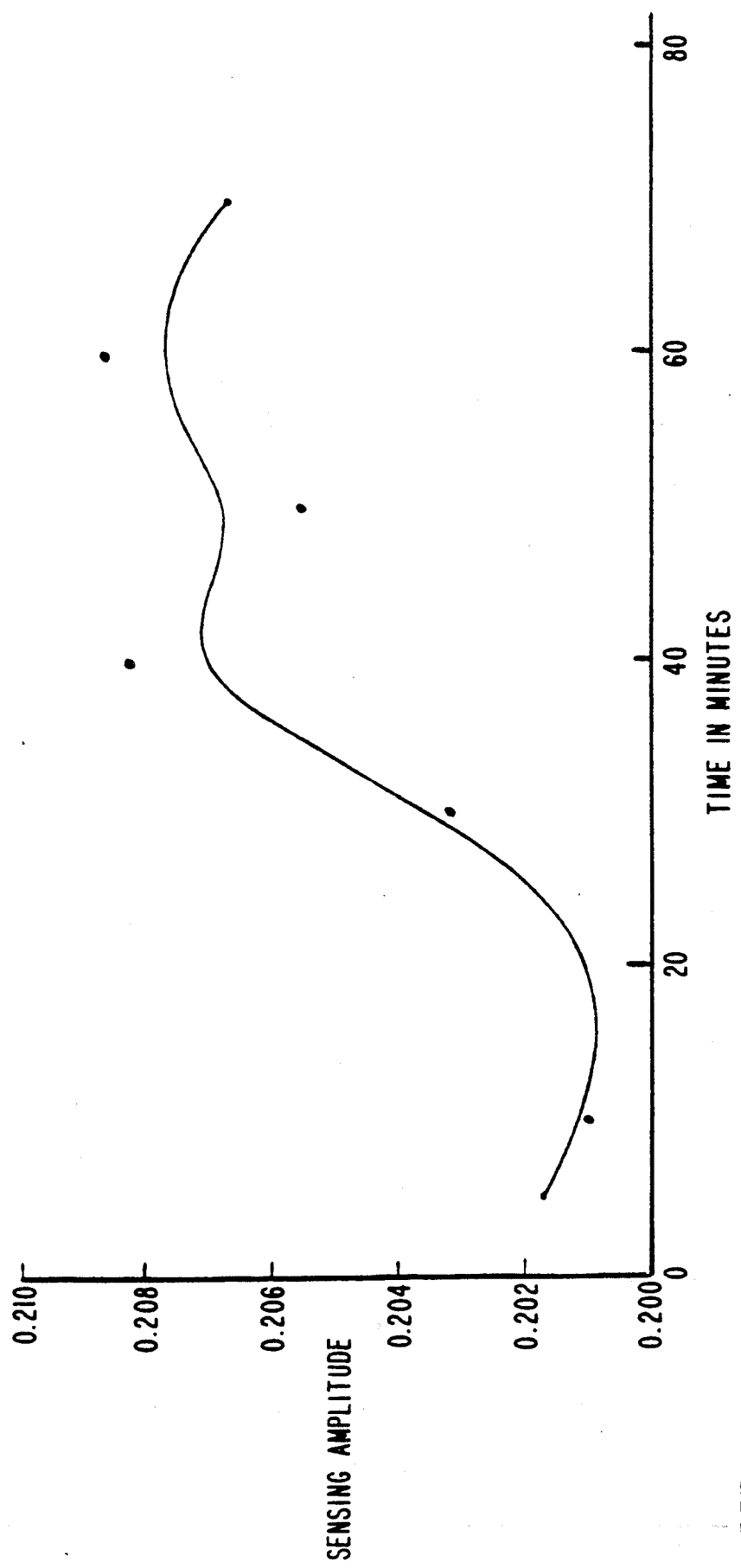
FIG. 11 is an expanded graph over a small range of wavelength presenting the response of the sensor as plotted in FIG. 10 over a time interval after the ingestion of glucose.

FIG. 11 is a graph showing the response of the sensor of the apparatus shown in FIG. 1 as a function of time as the ingested glucose is absorbed in the blood. Response is plotted vertically and time in minutes after ingestion horizontally. Initially, there is a decrease in the response. Then the response rises gradually to between 0.207 and 0.208 at about 40 minutes after ingestion. There is then a gradual small decrease at about 50 minutes and a further rise followed by a decrease.

Figure 12:
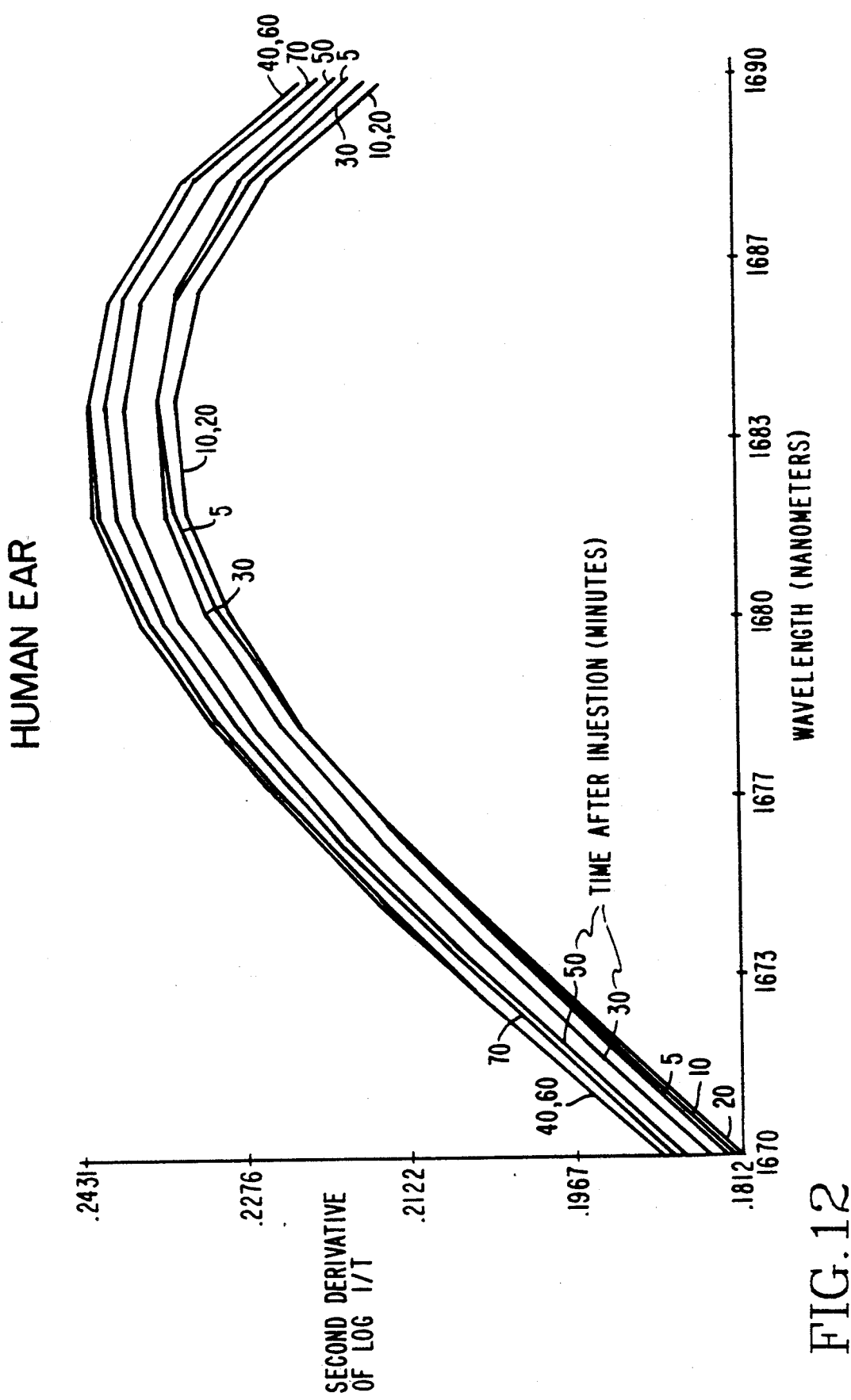
FIG. 12 is a graph of a family of curves, each curve plotted at a different time after injection of glucose, presenting the second derivative of the response (Log 1/T) of the sensor as a function of wavelength in the measurement of the transmission through the ear of the host.

In FIG. 12 the second derivative as a function of wavelength of log 1/T is plotted for the glucose concentration. The family of curves presents the second derivative function at different times in minutes after ingestion of the glucose. The curves are expanded over a narrow range between 1670 and 1690 nm. The curves of the family corresponding to the concentrations at different times in minutes after ingestion are labeled.

Figure 13:
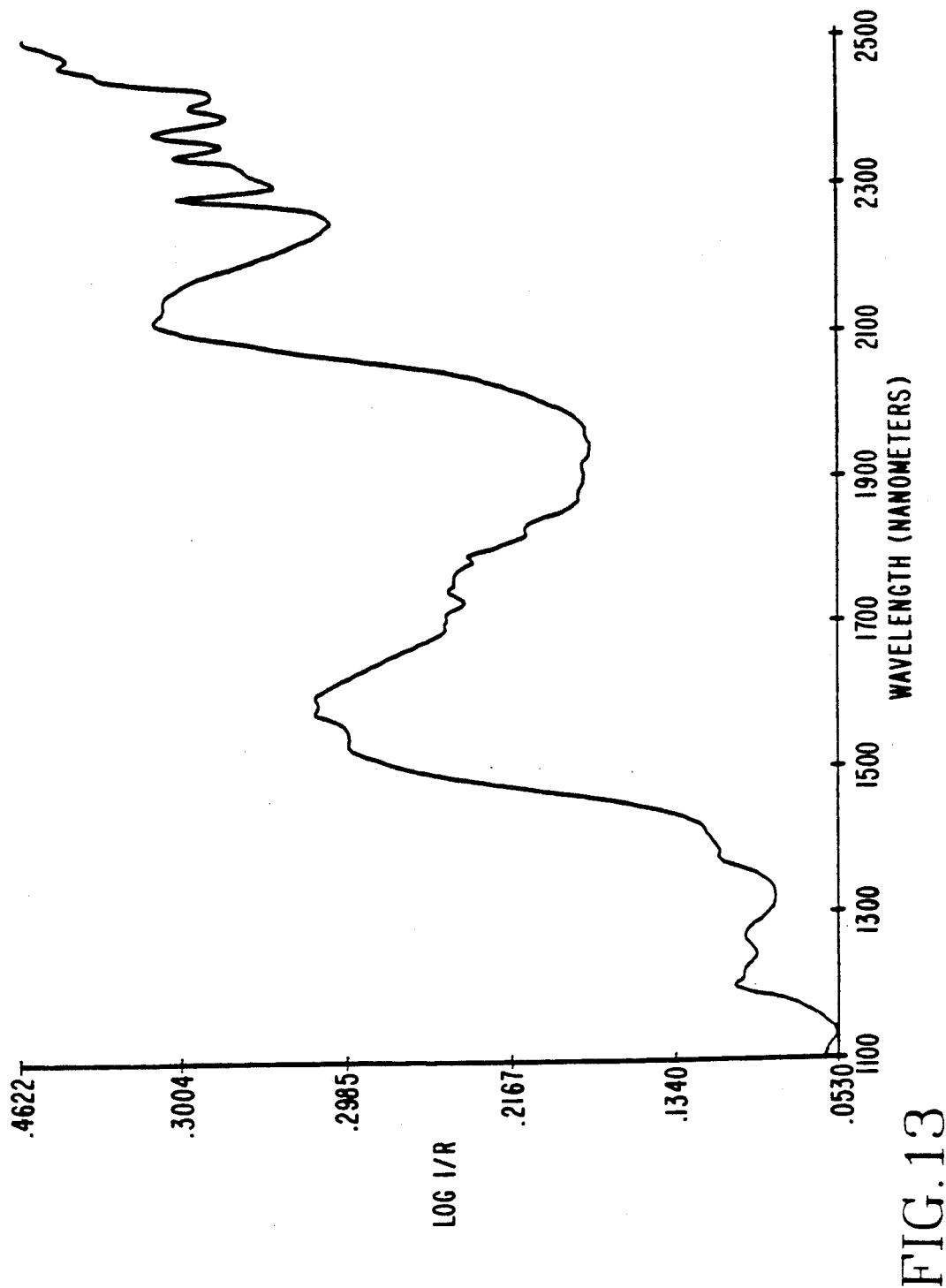
FIG. 13 is a graph presenting the log of the reciprocal of the reflection from solid glucose of radiation in the near infrared as a function of wavelength.

In FIG. 13, log 1/R is plotted as a function of wavelength for solid glucose. The data were derived by measuring the radiation scattered from the glucose by reflection. R is the intensity of the reflected radiation. The similarity between FIG. 13 and FIGS. 2, 7 and 10 is notable.

While a preferred embodiment and preferred practice of this invention has been disclosed herein, many modifications thereof are feasible. This invention is not to be restricted except insofar as is necessitated by the spirit of the prior art.

I claim:

1. The method of non-invasive determination of the concentration of glucose in a patient with apparatus including a source of radiation of wavelengths in the near infrared; the said method comprising: projecting radiation from said source on a portion of the body of said patient, varying the wavelengths of the radiation projected on said portion of said body over a limited range of wavelengths in the near infrared, sensing the resulting radiation emitted from said portion of said body, deriving from said sensed resulting radiation a first expression for the magnitude of said sensed radiation as a function of the wavelength to locate a region of said expression where the expression shows maximum influence by the portion of said body on the resulting radiation, responsive to the content of glucose in said patient of the portion of said body on the radiation incident on said portion of said body, deriving a second expression for the nth derivative of said function with respect to wavelength about a narrow range of wavelengths of the radiation of said region, producing an enlargement of said second expression over said narrow range of wavelengths, and determining said concentration of said glucose from the magnitude at a selected point of said enlargement of said second expression.

2. The method of non-invasive determination of the concentration of the glucose in a patient with apparatus including a source of radiation of wavelengths in the near infrared; said method comprising: projecting radiation of wavelengths in the near infrared on a portion of the body of said patient, varying the wavelength of said projected radiation over a narrow range of wavelengths about the wavelength of approximately 1660 nanometers, sensing the resulting radiation emitted from said portion of said body, deriving an expression for the magnitude of the resulting radiation as a function of the wavelength of said radiation, and determining said magnitude of the glucose by evaluating the nth derivative of said expression in an enlarged narrow range at about 1660 nanometers to determine the magnitude of the resulting radiation at the wavelength about 1660 nanometers at which the influence of said portion of said body on the radiation from said source incident thereon is a maximum, thereby to determine the concentration of the glucose in said patient.

3. The method of non-invasive determination of the concentration of glucose in a patient with apparatus including a source of radiation of wavelengths in the near infrared; the said method comprising: projecting from said source radiation of wavelength in the near infrared on a portion of the body of said patient, varying the wavelength of the radiation projected on said portion of said body over a limited range of wavelengths in the near infrared about the wavelength of approximately 1660 nanometers, sensing the resulting radiation emitted by said portion of said body to derive an expression which is a measure of the magnitude of said resulting radiation as a function of the wavelength of the impinging radiation having a stationary point in the region of 1660 nanometers, deriving the nth order derivative of said expression over a narrow range of wavelengths immediately in the region of 1660 nanometers, and determining the concentration of the glucose from said stationary point of said nth order derivative.

4. The method of claim 1 wherein the narrow range is between about 1640 and 1670 nanometers.

5. The method of claim 3 wherein the limited range is between about 1100 and 1900 nanometers and the narrow range is between about 1640 and 1670 nanometers.

6. The method of claim 2 wherein the narrow range is between about 1640 nanometers and 1670 nanometers.

7. The method of claim 3 wherein the nth derivative is the second derivative.

8. The method of claim 1 wherein the nth derivative is the second derivative.

9. Apparatus for non-invasive determination of the concentration of glucose in a patient including: a source of infrared radiation, a first fiber-optic conductor of radiation adapted to be connected to an external surface of a portion of the body of said patient, means positioning said first fiber-optic conductor to transmit radiation from said source to said portion through said surface as incident radiation thereon, a second fiber-optic conductor of radiation adapted to be connected to an external surface of said portion of the body of the patient to transmit radiation emitted from said portion resulting from the impingement of said incident radiation, first deriving means, connected to said second fiber-optic conductor, to derive from said resulting radiation a first continuous expression defining the magnitude of said resulting radiation as a function of wavelength of said radiation and a second deriving means, connected to said first deriving means, for deriving from the first expression a second expression defining the nth derivative of the first expression as a function of wavelength of the radiation, and means, connected to said second deriving means, for processing the resulting radiation from said portion in dependence upon said continuous expression to determine said concentration.

10. The apparatus of claim 9 wherein the deriving means includes means for scanning the resulting radiation continuously over a predetermined range of wavelengths and means, responsive to said scanning means, to derive the expression.

11. The apparatus of claim 9 wherein the deriving means includes a spectrum analyzer for analyzing the spectrum of the resulting radiation emitted by the portion of the body of the patient and also includes means, connected to said analyzer, for deriving the expression for said resulting radiation as a function of the wavelength.

12. The apparatus of claim 9, the processing means includes second deriving means, connecting wherein processing means is controlled by the second expression to determine the concentration.

13. The method of non-invasive determination of the concentration of glucose in a patient with apparatus including a source of radiation of wavelengths in the near infrared; the said method comprising: projecting radiation from said source on a portion of the body of said patient, varying the wavelengths of the radiation projected on said portion of said body over a limited range of wavelengths in the near infrared, sensing the resulting radiation emitted from said portion of said body, deriving from said sensed resulting radiation a first expression for the magnitude of said sensed radiation as a function of the wavelength to locate a region of said first expression where said expression shows maximum influence by the portion of said body on the resulting radiation responsive to the content of glucose in said patient on the radiation incident on said portion of said body, deriving a second expression for the nth derivative of said expression with respect to wavelength about a narrow range of wavelengths of said region, and determining said concentration of said glucose from the magnitude of said second expression at a selected point of said narrow range.

* * * * *

UNITED STATES PATENT AND TRADEMARK OFFICE
CERTIFICATE OF CORRECTION

PATENT NO. : 5,070,874
DATED : December 10, 1991
INVENTOR(S) : Russell H. Barnes, et al It is certified that error appears in the above-identified patent and that said Letters Patent is hereby corrected as shown below:

On the Title page, item [75], please add the following:

--David L. Purdy, Marion Center, PA--
--William D. Lougheed, Ontario, Canada--

Signed and Sealed this

Twentieth Day of July, 1993

Attest:

MICHAEL K. KIRK

Attesting Officer    Acting Commissioner of Patents and Trademarks